(12) United States Patent
Hubert et al.

(10) Patent No.: US 6,626,668 B2
(45) Date of Patent: Sep. 30, 2003

(54) MEDICAL OR DENTAL-MEDICAL APPARATUS HAVING A DELIVERY LINE FOR A LIQUID

(75) Inventors: Mösslang Hubert, Oberdischingen (DE); Wiest Gebhard, Hochdorf (DE); Wenger Georg, Schemmerhofen (DE); Eberle Jörg, Mittelbiberach (DE)

(73) Assignee: Kaltenbach & Voigt GmbH & Co., Biberach (DE)

( * ) Notice: Subject to any disclaimer, the term of this patent is extended or adjusted under 35 U.S.C. 154(b) by 99 days.

(21) Appl. No.: 09/989,642

(22) Filed: Nov. 20, 2001

(65) Prior Publication Data

US 2002/0090590 A1 Jul. 11, 2002

(30) Foreign Application Priority Data

Jan. 5, 2001 (DE) ......................................... 101 00 361

(51) Int. Cl.$^7$ ............................................... A61G 17/02
(52) U.S. Cl. ..................... 433/80; 141/291; 141/293; 141/301; 141/384; 215/309
(58) Field of Search ............................. 433/80, 81, 82, 433/83, 84, 85, 86, 88; 215/309, 311, 313, 314, 315; 141/147, 291, 292, 293, 294, 301, 308, 384, 386

(56) References Cited

U.S. PATENT DOCUMENTS

| | | | | |
|---|---|---|---|---|
| 2,661,537 A | * | 12/1953 | Angell | 433/88 |
| 4,054,133 A | * | 10/1977 | Myers | 128/142.2 |
| 4,235,269 A | * | 11/1980 | Brake et al. | 141/293 |
| 4,830,210 A | | 5/1989 | Mabille | 215/309 |
| 4,836,414 A | | 6/1989 | Credle, Jr. et al. | 222/1 |
| 5,425,404 A | * | 6/1995 | Dyer | 141/351 |
| 5,503,553 A | | 4/1996 | Hines | 433/80 |
| 5,836,483 A | * | 11/1998 | Disel | 222/396 |
| 5,848,622 A | * | 12/1998 | Kilcoin | 141/59 |
| 5,927,977 A | | 7/1999 | Sale et al. | 433/86 |

* cited by examiner

Primary Examiner—John J. Wilson
(74) Attorney, Agent, or Firm—Marshall, Gerstein & Borun

(57) ABSTRACT

The invention relates to a medical or dental-medical apparatus, having a delivery line for a liquid and having a screw bushing onto which a container for the liquid can be screwed, the delivery line extending from the interior of the container to the outside and penetrating the screw bushing, a compressed gas line penetrating the screw bushing from the outside inwardly, and the compressed gas line being closable and openable by means of a valve. In order to simplify the operating effort, the screw bushing is rotatably mounted in a rotary bearing and is in working connection with a switch cam which, in a rotary position of the screw bushing which is rotated in the screwing-on direction, opens the previously closed valve.

18 Claims, 2 Drawing Sheets

US 6,626,668 B2

MEDICAL OR DENTAL-MEDICAL APPARATUS HAVING A DELIVERY LINE FOR A LIQUID

FIELD OF THE INVENTION

The invention relates to a medical or dental-medical apparatus of the type having a container for liquid, a delivery line for a liquid extending from the interior of the container through a screw bushing, and a compressed gas line extending into the gas container from the outside thereof through the screw bushing.

The invention relates to a medical or dental-medical apparatus in accordance with the preamble of claim 1.

BACKGROUND OF THE INVENTION

When working with an apparatus of the kind concerned a liquid is needed which in functional operation is supplied through a delivery line to the treatment or working site. In the case of an apparatus for the treatment of the human or animal body there is needed a liquid which is safe from a health point of view. If a liquid of this quality, e.g. from the public water supply, is not available, it is known to take the liquid from a container, a so-called water bottle, associated with the treatment apparatus. For this purpose there serves a connection device for the container having a screw bushing into which the container is screwed from below with a threaded connection piece, for its connection. Before the screwing, an inlet end of the delivery line, projecting downwardly beyond the screw bushing is to be introduced into the opening of the container. Further, the apparatus has a compressed gas line which ends in the region of the screw bushing and in which a first valve for opening and closing the compressed gas line is arranged. After the screwing on of the container filed with liquid, the valve is manually opened so that the compressed gas enters into the container and can place the liquid located there under pressure, which flows out through the delivery line when a second valve arranged in the region of the delivery line is opened. For a dismounting or for an exchange of the container it is necessary to manually close the valve before screwing off the container. Upon screwing off of the container, the gas pressure still present in the container is released and a filled container can be mounted.

SUMMARY OF THE INVENTION

The object of the present invention is so to configure a medical or dental-medical apparatus such that the operating effort is reduced.

This object is achieved by means of the features of claim 1. Advantageous developments of the invention are indicated in the subclaims.

With the apparatus in accordance with the invention the screw bushing is rotatably mounted on a container carrier in a rotary bearing and it has a cam which in the rotary end position, directed in the screw-in direction, opens the previously closed valve. By these means, upon connection of the container, the valve is automatically opened and the container placed under pressure, so that the liquid located therein is ready, after an opening of the second valve, to flow out of the instrument. A special manual measure for opening the first valve is not necessary. The configuration in accordance with the invention thus makes possible a significant reduction of the operational effort. Furthermore, the risk is removed that it would be forgotten to open the first valve, which would lead to considerable disruption in a subsequent use of the apparatus.

It is further of advantage to so configure the first valve that upon its closure a venting of the container interior is made possible. By these means there is no escape of compressed gas upon screwing off and no noises arising therefrom.

BRIEF DESCRIPTION OF THE DRAWINGS

Below, advantageous configurations of an exemplary embodiment in accordance with the invention will be described in more detail with reference to the drawings, which show.

DETAILED DESCRIPTION OF THE INVENTION

Figure 1:
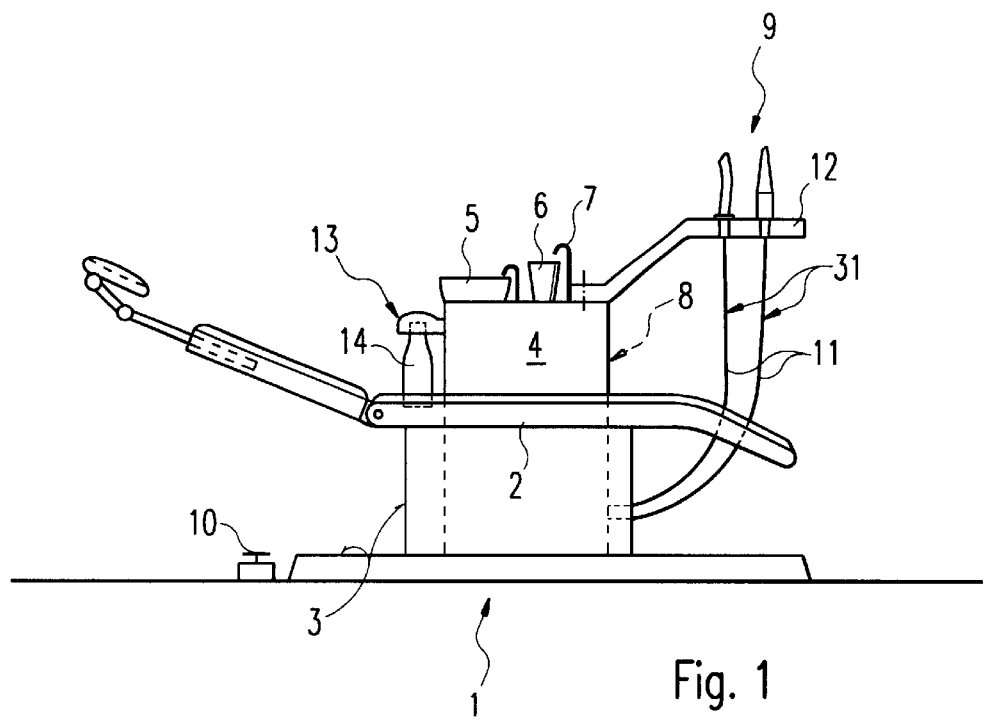
FIG. 1 a medical or dental-medical apparatus in the form of a treatment chair having a connection device for a container, in a side view.

The main parts of the apparatus or treatment chair, designated as a whole with 1, are a patient seat 2, having a backrest and also a head support, which is in particular mounted height-adjustably on a chair base 3. Next to the patient seat 2 there are arranged on a housing 4, a cuspidor 5 with a rinsing arrangement and a water beaker 6 with a tap 7 for water. There is installed in the housing 4 a supply arrangement, designated overall with 8. Further, one or more treatment instruments 9, e.g. having a spray handpiece and a drill handpiece, are provided which are in each case connected with the supply arrangement 8 by means of a flexible supply line 11 and can be deposited at or on a repository device 12 which is preferably mounted horizontally pivotably, e.g. on the housing 4. For switching on and switching off various functions of the apparatus 1, e.g. drill drive or spray of a treatment liquid out of the treatment instrument 9, there is provided a switch 10, e.g. a foot switch.

In or on the housing 4 there is arranged at a readily accessible location a connection device 13 for a container 14 which constitutes a reservoir for the treatment liquid and after emptying through use during patient treatments is replaced by a full container 14.

Figure 2:
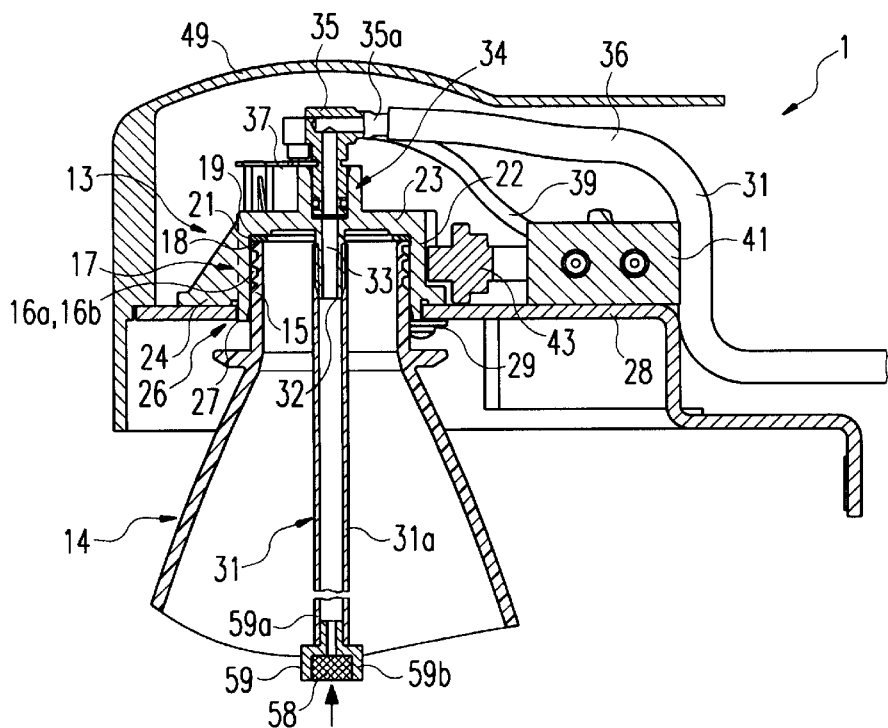
FIG. 2 the connection device, in a sectional illustration to an enlarged scale.

The container 14 has, in accordance with FIG. 2, at its upper end an approximately vertical threaded connecting piece 15 having an external thread 16a which is preferably a double-start thread. The connection device 13 has a screw-in bushing 17, open downwardly, having an internal thread 16b into which the threaded connecting piece 15 can be so far screwed that a shoulder 18 on the container 14 closely bears on a shoulder 19 on the screw-in bushing 17, e.g. with the intermediate mounting of a sealing ring 21. With the present exemplary embodiment, the shoulder 18 is formed by means of the upper edge of the threaded connection piece 15 and the counter-shoulder 19 is formed by means of the floor of the screw-in recess of the screw-in bushing 17. The screw-in bushing 17 has the form of an upturned pot with a peripheral wall 22, a ceiling wall 23 and a flange 24 on the lower side, which with the peripheral wall 22 may be stabilized by means of reinforcement ribs 25.

The screw-in bushing 17 is freely rotatably mounted in a rotary bearing 26, which e.g. is formed by means of an approximately vertical bore 27 in a plate-like carrier part 28 into which bore the screw-in bushing 17 engages from above with the lower edge of its peripheral wall 22 and engages therebelow with a securing part 29 attached thereto.

From the lower side of the ceiling wall 23 there extends downwardly a delivery line section 31a in the form of a tube or flexible hose, which is so long that it extends as far as the floor region of the screwed-on container 14, and which forms the beginning end of the delivery line 31 for the supply of liquid to the at least one treatment instrument 9. The delivery line section 31a may be plugged on to or a screwed on to a connection piece 32 projecting downwardly from the ceiling wall 23. From the connection piece 32 there extends a channel 33, through the ceiling wall 23, and a plug-in coupling 34, arranged on the upper side of the ceiling wall 23, having a cylindrical plug recess and a cylindrical plug pin inserted therein from above with play for movement, which plug pin is arranged in a plug coupling part 35 which extends straight or angled, which plug coupling part has at it end opposite to the plug pin a connection piece 35a which is connected with a connection line 36 in the form of a tube or a flexible hose, e.g. by being pushed thereon, which is connected at its other end with the treatment instrument 9 or extends to the treatment site at the patient and likewise forms the delivery line 31. A longitudinal arresting of the plug pin in the plug recess can be formed by means of a securing disk 37 which is attached to the upper side of the screw-in bushing 17 and engages into a ring groove worked into the outer surface of the plug pin. The plug coupling ensures a free rotatability, in the sense of the rotary coupling, between the screw-in bushing 17 and the plug pin. Therefore, the screw-in bushing 17 can be rotated without the connection line 36 having to rotate therewith. This can thus be of a non-flexible pipeline. It may, however, also be flexible, e.g. be formed by a hose.

In similar manner, a pressure line 39 for a flowable pressure medium, in particular compressed air, may be connected with the screw-in bushing 17. In order to avoid repetition, attention is therefore directed to the description of the connection of the connection line 36. The pressure line 39 does not, however, need to extend as far as the floor region of the container 14, since it needs merely to open out in the upper region of the interior of the container 14 in order to place the interior under over-pressure. A pressure channel, penetrating the ceiling wall 23 and standing in connection with the pressure line 39, is present but hidden in FIG. 1 and therefore not illustrated. Therefore, also the pressure line 39 may be formed by means of a rigid pipeline section or a flexible hose.

Figure 3:
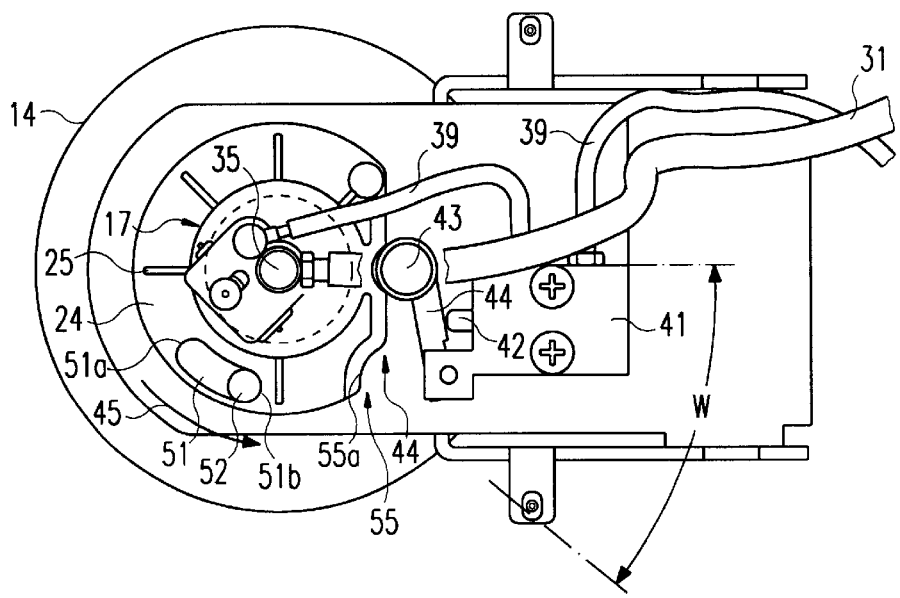
FIG. 3 the connection device, in a view from above.
Figure 4:
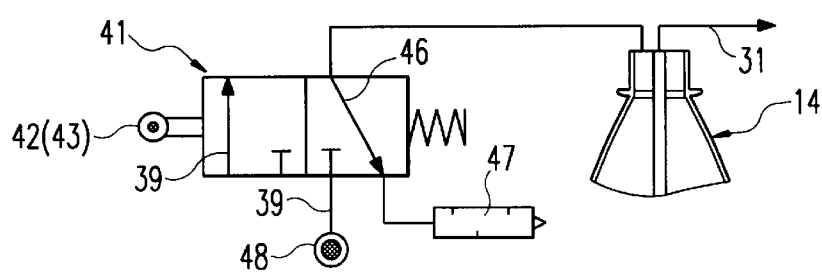
FIG. 4 a schematic functional plan for a first valve in a gas pressure line, which shows the interior of the container in its working disposition connected with the connecting device.

In the pressure line 39 there is arranged a valve 41 which in its initial disposition is in the closed position and which can be opened by means of the displacement of its valve cam 42. A pilot cam 43 on a cam arm 44, which acts against the valve cam 44, may be provided before the valve cam 42. The valve cam 42 or the pilot cam 43 cooperate with a switching cam 44 arranged on the periphery of the screw-in bushing 17 in such a manner that in the rotary initial position of the screw-in bushing 17 in accordance with FIG. 3 the pilot cam 43 or the valve cam 42 are located in their released position, in which the pressure line 39 is closed. Upon screwing-in of the container 14 the screw-in bushing 17 is rotated in the direction of the arrow 45, whereby the switch cam 44 displaces the valve 41 into its open position. Preferably, the valve 41 also has a venting channel 46 which in the closed position of the valve 41 connects the container interior with the surroundings, for the purpose of venting. The valve 41 may be formed by means of a 3/2-way valve, which is illustrated in FIG. 4 in its position closing the pressure line 39, in which the venting channel 46 is open for venting the container interior and is preferably connected with a sound damper 47. In FIG. 4, a pressure source for pressure gas, in particular for compressed air, is designated with 48. The valve 41 may be arranged on the carrier part 28 next to the screw-in part 17 and e.g. be bolted on. As FIG. 2 clearly shows, the connecting device 13 may be covered over by means of a protective cap 49 placed on the carrier part 28. The overpressure in the container 14 can, however, also escape through the thread engagement upon screwing loose, so that a venting channel 46 can be omitted.

The free rotatability of the screw-in bushing 17 is preferably so restricted by means of respective stops that it can be rotated solely between its initial rotary position and its final rotary position. For this purpose there may serve a curved longitudinal hole 51, preferably in the flange 24, through which a stop pin 52 extends and bounds the above-described movements thereof. The stop pin 52 may be arranged e.g. on the carrier part 28 and stand upwardly therefrom. Thereby, the stops are formed by means of the longitudinal hole ends 51a, 51b.

Upon joining the container 14 to the connection device 13, here the screw-in bushing 17, there is needed a certain torque M1, which is necessitated on the one hand through the friction upon screwing and on the other hand through an axial pressure of the threaded connection piece 15 on the seal 21. This torque M1 can readily be applied by manually grasping the container 14. In order to prevent that the screw-in bushing 17 rotates upon screwing on of the container 14 and actuates the valve 41, for the purpose of pressure connection, before the threaded connection piece 15 is sealingly connected with the screw-in bushing 17, the rotary bearing 26 is so formed that the screw-in bushing 17 is rotatable therein only with a torque M2 which is greater than the above-mentioned torque M1. The torque M2 is likewise dimensioned so great that it can be manually produced without problem. As a consequence, upon connection of a container 14, the container 14 is initially sealingly connected with the screw-in bushing 17 and then by means of further manual turning the screw-in bushing 17 is turned out of its initial rotary position into its final rotary position, in which the valve 41 is actuated and the container 14 acted on with pressure. The action with pressure effects an increase of the connecting forces effective between the container 14 and the screw-in bushing 17. Under pressure, the container 14 can be released by screwing off only with a torque M3, which likewise can be manually applied without problem, which is greater than the above-mentioned torque M2.

Figure 5:
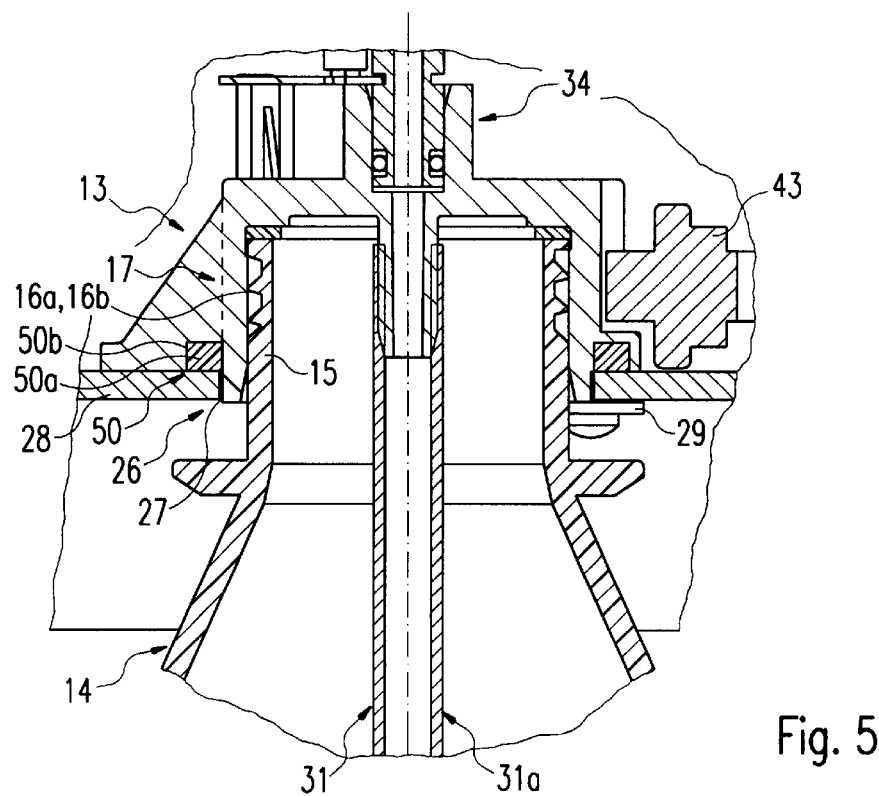
FIG. 5 the connecting device in accordance with FIG. 2 in a modified consideration, and in a sectional illustration to an enlarged scale.

The torque M2 can be attained e.g. by means of a stiffness in the rotary bearing 26 or by means of a brake, the braking force of which is preferably adjustable. With the exemplary embodiment according to FIG. 5, in which the same or similar parts are provided with the same reference signs, such a brake 50 is present and preferably integrated into the rotary bearing 26. The brake 50 has a preferably annular brake element 50a, which is arranged on a part of the rotary bearing 26, here on the screw-in bushing 17, preferably in an angular groove 50b, e.g. in the flange 24. The brake element 50a can be formed by means of a ring of elastic material, e.g. rubber or plastics. With the present exemplary embodiment, the axial cross-sectional dimension of the brake element 50a is dimensioned to be so great that in the functional position illustrated in FIG. 5 the brake element 50a is axially elastically compressed and thereby pressed against the other rotary bearing part with an elastic braking force. By these means, the torque M2 is secured. In order to be able to adapt the torque M2 to a particular value, it is advantageous to form the preferably axial biasing force, with which the friction parts concerned are biased against one another, adjustably. With the present exemplary embodiment this can be achieved in that the securing part 29, e.g. an edge flange engaging below the edge of the bearing bore 27, is axially adjustable and is fixable in the adjusted position, e.g. is screwable or adjustable with a screw thread.

Within the scope of the present invention, the connection device 13 is also then capable of functioning when the screw-in bushing 17 is freely rotatably mounted; that is, is formed without brake or stiffness. In such a case it is possible to hold the screw-in sleeve 17, upon joining of the container 14, manually in the initial rotary position. In such a case, however, a two-handed operation would be necessary, whilst with the presence of a brake or stiffness, one-hand operation is possible.

In order, in the absence of a brake or stiffness, to avoid that the screw-in bushing 17 remains in its rotary end position and does not turn back with the container 14, which e.g. can be brought about by vibrations during functional operation of the apparatus 1, it is advantageous to associate with the screw-in bushing 17 in its final rotary position a positioning device 55 which prevents an undesired return rotation. Preferably, the positioning device 55 is formed by means of an elastically effective latching device, the spring force of which is only so great that the latching is overcome upon screwing-in and screwing-out of the container 14 and the thereby occurring rotation of the screw-in bushing 17. With the present exemplary embodiment, the positioning device is formed by means of a latch depression 55a on the switch cam 44 into which the valve cam 42 or pilot cam 43, standing under spring pressure, latch and upon return rotation are self-actingly pressed out. The positioning device may also be present with a brake or stiffness as is the case with the exemplary embodiment according to FIG. 5.

Below, an exchange of the container 14 will be described by way of example as follows. The container 14, connected by means of the connection device 13, is manually turned in the release direction, whereby due to the effective torque M3 the screw-in sleeve 17 is also rotated from the final rotary position to the initial rotary position.

Thereby, the switch cam 44 releases the valve cam, whereby the valve 41 self-actingly closes the pressure line 39 due to the valve spring present. In this rotary position, the screw-in bushing 17 is limited in its rotary movement by means of the pin 52 forming a stop. The rotary angle W of this rotary movement is less than 360°. An angle of 180 or 90° is more advantageous in order to reduce the effort for rotation. With the configuration in accordance with the invention, the rotary angle W is less than 90°, in particular only about 45°. Already in this rotary position, in which the thread engagement has not yet been turned, the interior of the container 14 is vented through the venting line 46 of the valve 41.

With further screwing loose of the container 14, the thread engagement is released through screwing out and a new container 14, filled with treatment liquid, can be screwed in. Upon screwing in, after screwing fast, the screw-in bushing 17 is rotated into the opposite stop position, namely into the final rotary position, whereby the switch cam 44 opens the valve 41 and the pressure in the pressure line 39 can enter the container interior, so that this is ready for a release of the treatment liquid. By means of an opening of a non-illustrated second valve in the delivery line 31, which in each case extends through the flexible supply line 11, the issue of the treatment liquid can be controlled from the treatment instrument 9, e.g. by means of a foot switch 10, which the operating or treating person actuates.

In order to protect the delivery line 31 from contamination, it is advantageous to arrange a sieve or filter 58 therein, which serves to sieve or filter the liquid flowing into the delivery line 31 out of the container interior under the effect of pressure. With the present exemplary embodiment, a sieve or filter 58 is arranged at the inlet end of the delivery line 31 or of the hose 31a. Preferably, a sleeve-like bushing 59 is provided which can be inserted in a clamping manner into or onto the delivery line 31 with a tapered pin 59a, and has a bushing 59b, enlarged in section, in which the sieve or filter 58 is fixedly placed. By these means there is formed a cartridge which can be economically manufactured and can be mounted, which as a prefabricated component and exchangeable part can be readily and rapidly mounted or dismounted.

What is claimed is:

1. Medical or dental-medical apparatus comprising a delivery line for a liquid and a screw bushing onto which a container for the liquid can be screwed, the delivery line extending from the interior of the container to the outside and penetrating the screw bushing, a compressed gas line penetrating the screw bushing from the outside, the compressed gas line being closable and openable by means of a valve, wherein the screw bushing is rotatably mounted in a rotary bearing and is in working connection with a switch cam which, in a rotary position of the screw bushing which is rotated in a screwing-on direction, opens the previously closed valve.

2. Medical or dental-medical apparatus according to claim 1, wherein the rotary movement of the screw bushing is bounded at an initial rotary position and a final rotary position.

3. Medical or dental-medical apparatus according to claim 1, wherein the valve has a venting channel for venting the interior of the container in its closed position.

4. Medical or dental-medical apparatus according to claim 1, wherein at least one of the delivery line and the compressed gas line is connected with the screw bushing by means of a coaxially and/or axis-parallel arranged rotary coupling.

5. Medical or dental-medical apparatus according to claim 4, wherein at least one of the delivery line and the compressed gas line comprises a flexible line.

6. Medical or dental-medical apparatus according to claim 1, wherein the switch cam is arranged on the screw bushing.

7. Medical or dental-medical apparatus according to claim 6, wherein the switch cam is arranged at the periphery of the screw bushing.

8. Medical or dental-medical apparatus according to claim 1, wherein the rotary bearing is stiff or has a brake having a torque which is greater than a torque transferred to the screw bushing upon connection of the container by means of rotation.

9. Medical or dental-medical apparatus according to claim 8, wherein the size of the braking force is adjustable by means of an adjustment element.

10. Medical or dental-medical apparatus according to claim 1, further comprising a positioning device for positioning the screw bushing in its final rotary position.

11. Medical or dental-medical apparatus according to claim 10, wherein the positioning device is formed by means of a latching device.

12. Medical or dental-medical apparatus according to claim 11, wherein has a latch depression on the switch cam into which the valve cam latches.

13. Medical or dental-medical apparatus according to claim 11, wherein the latching device can be overcome with manual turning.

14. Medical or dental-medical apparatus according to claim 1, wherein the screw bushing has the shape of an upturned pot.

15. Medical or dental-medical apparatus according to claim 14, wherein the screw bushing has a flange and the switch cam is formed on the flange.

16. Medical or dental-medical apparatus according to claim 14, wherein the rotary bearing is arranged at the lower edge of a peripheral wall of the screw bushing.

17. Medical or dental-medical apparatus according to claim 1, wherein the screw bushing is rotatable through a maximum rotary angle of less than 360°.

18. Medical or dental-medical apparatus according to claim 17, wherein the screw bushing is rotatable through a maximum rotary angle of less than 90°.

* * * * *